US009566145B2

(12) United States Patent
Trainor et al.

(10) Patent No.: US 9,566,145 B2
(45) Date of Patent: Feb. 14, 2017

(54) IMPLANTABLE DEVICE FOR DIRECTIONAL CONTROL OF FLOW WITHIN THE ANATOMIC TRACTS OF THE BODY

(71) Applicants:The Charles Stark Draper Laboratory, Inc., Cambridge, MA (US); The Brigham and Women's Hospital, Inc., Boston, MA (US)

(72) Inventors: Christopher V. Trainor, Boxborough, MA (US); Ali Tavakkoli, Boston, MA (US); Jeffrey Ishizuka, Boston, MA (US); Daniel F. Traviglia, Waltham, MA (US); William McFarland, Waltham, MA (US)

(73) Assignees: The Charles Stark Draper Laboratory, Inc., Cambridge, MA (US); The Brigham and Women's Hospital, Inc., Boston, MA (US)

( * ) Notice: Subject to any disclaimer, the term of this patent is extended or adjusted under 35 U.S.C. 154(b) by 214 days.

(21) Appl. No.: 13/955,396

(22) Filed: Jul. 31, 2013

(65) Prior Publication Data

US 2014/0039641 A1    Feb. 6, 2014

Related U.S. Application Data

(60) Provisional application No. 61/677,800, filed on Jul. 31, 2012.

(51) Int. Cl.
*A61F 2/04* (2013.01)
*B29C 33/42* (2006.01)
(Continued)

(52) U.S. Cl.
CPC ............... *A61F 2/04* (2013.01); *B29C 33/424* (2013.01); *A61F 2/24* (2013.01); *A61F 2002/0081* (2013.01); *A61F 2002/044* (2013.01)

(58) Field of Classification Search
CPC ............... A61F 2/04; A61F 2/82; A61F 2/24; A61F 2002/044; A61F 2002/046; A61F 2002/0081; A61M 5/168; A61M 5/16881; B29C 33/424
See application file for complete search history.

(56) References Cited

U.S. PATENT DOCUMENTS 5,002,572 A * 3/1991 Picha .................. 623/23.74
2001/0020189 A1   9/2001 Taylor
(Continued)

FOREIGN PATENT DOCUMENTS

GB      1 354 691 A       5/1974
WO      WO-02/094132 A2   11/2002
WO      WO-2007/072469 A2 6/2007

OTHER PUBLICATIONS

International Search Report and Written Opinion mailed Oct. 24, 2013 in PCT Application No. PCT/US2013/052910 (12 pages).

*Primary Examiner* — David Isabella
*Assistant Examiner* — Rokhaya Diop
(74) *Attorney, Agent, or Firm* — McDermott Will & Emery LLP

(57) ABSTRACT

The systems and methods described herein related generally to a device that enables the directional control of flow through an anatomical tract of the body. More particularly, the device described herein includes a valve from a plurality of projections. In some implementations, the projections are configured as flaps, posts, or any combination thereof. In some implementations, the device is implanted into a patient's esophagus to prevent gastroesophageal reflux disease. The plurality of projections allow flow into a patient's (Continued)

stomach while substantially preventing a backflow of undesired fluids from the patient's stomach to the patient's esophagus.

12 Claims, 14 Drawing Sheets

(51) Int. Cl.
*A61F 2/24* (2006.01)
*A61F 2/00* (2006.01)

(56) References Cited

U.S. PATENT DOCUMENTS

| | | |
|---|---|---|
| 2003/0060894 A1 | 3/2003 | Dua et al. |
| 2003/0069646 A1* | 4/2003 | Stinson ............... 623/23.7 |
| 2005/0027348 A1* | 2/2005 | Case ............... A61F 2/2412 623/1.24 |
| 2005/0165356 A1* | 7/2005 | Pasqualucci ............ 604/167.06 |
| 2005/0228505 A1 | 10/2005 | Cornet et al. |
| 2006/0257444 A1 | 11/2006 | Tropsha et al. |
| 2007/0208429 A1 | 9/2007 | Leahy |
| 2009/0118712 A1 | 5/2009 | Carter et al. |
| 2010/0121461 A1* | 5/2010 | Sobrino-Serrano et al. ............ 623/23.68 |
| 2010/0137891 A1 | 6/2010 | Shalon et al. |
| 2010/0256775 A1 | 10/2010 | Belhe et al. |
| 2012/0089236 A1* | 4/2012 | Errico et al. ............ 623/23.68 |
| 2012/0184893 A1 | 7/2012 | Thompson et al. |
| 2012/0283842 A1 | 11/2012 | Sobrino-Serrano et al. |
| 2013/0304231 A1 | 11/2013 | Errico et al. |

* cited by examiner

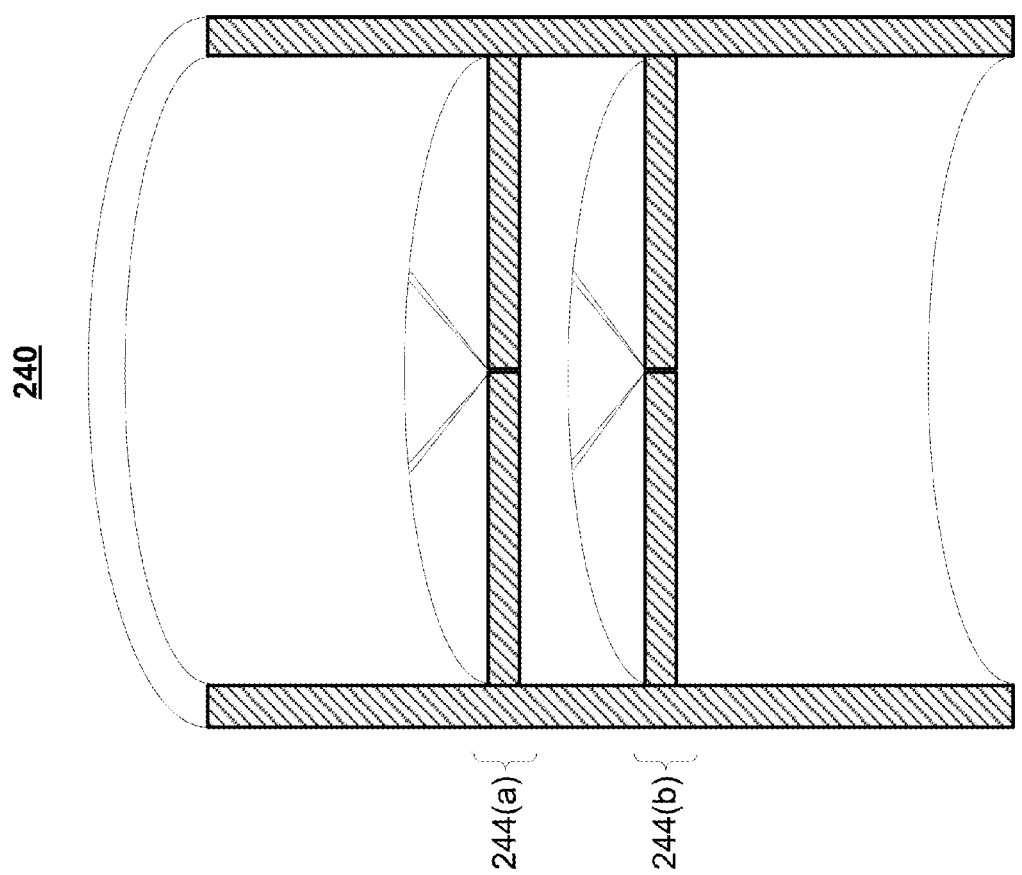

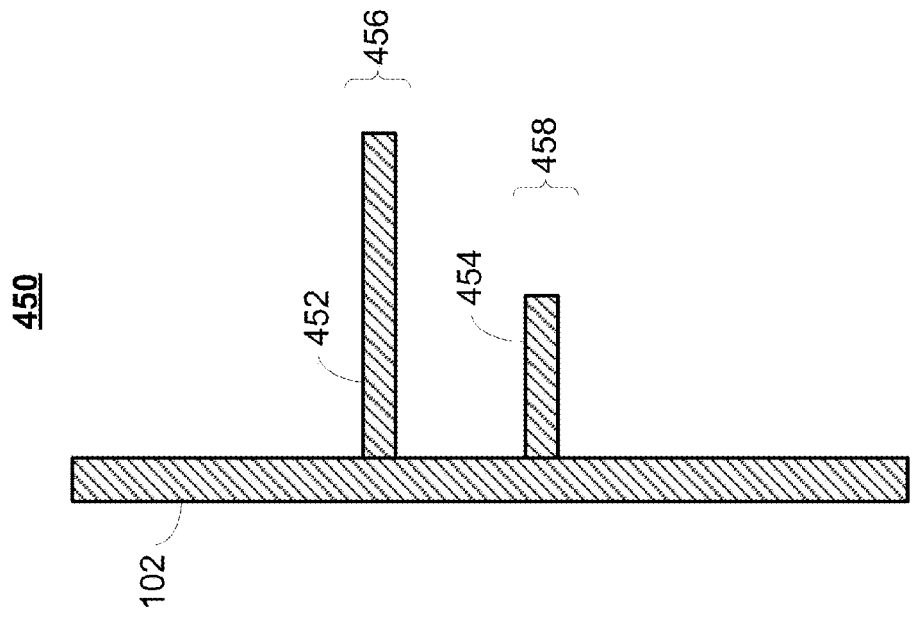
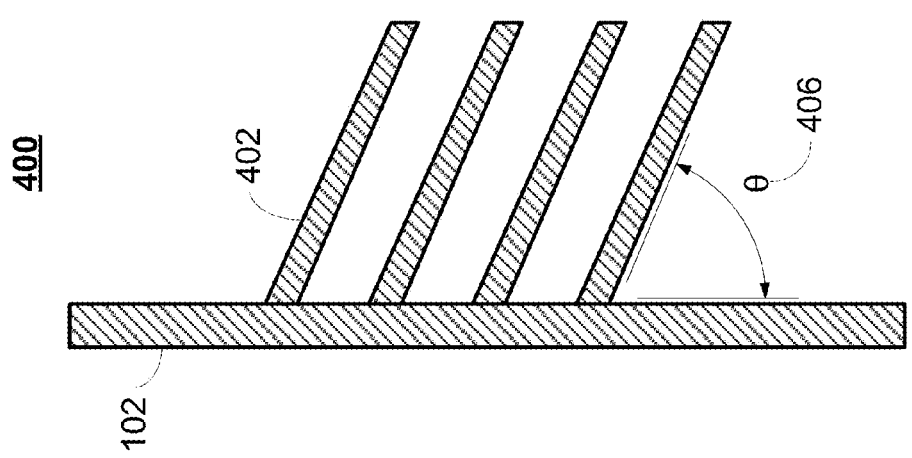
Figure 4B
Figure 4A

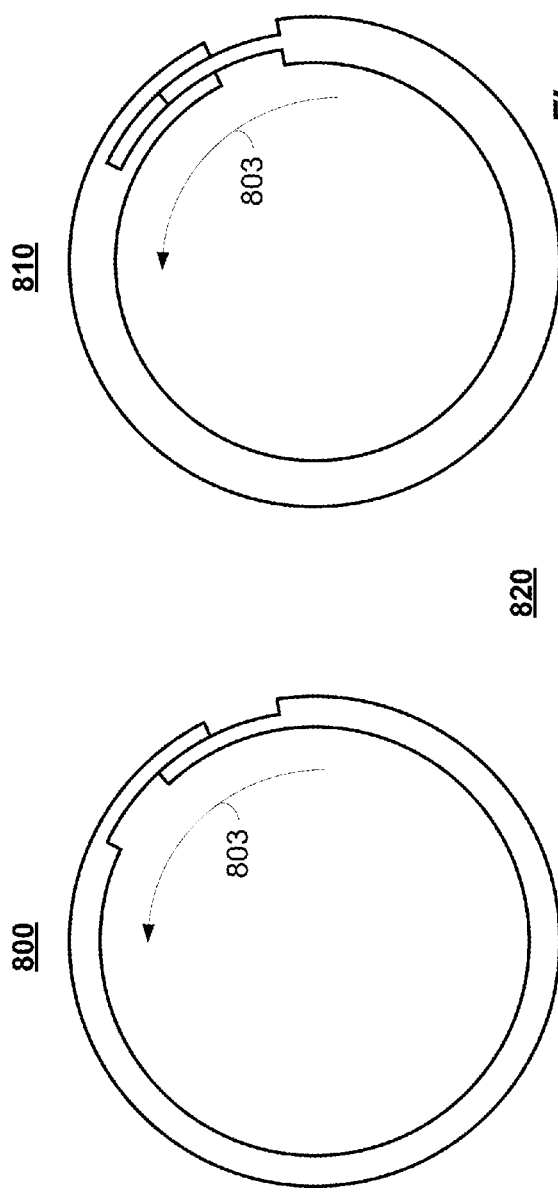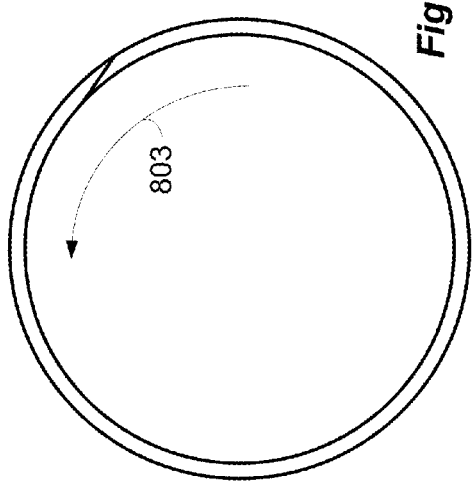

ial control of flow through an anatomic tract of a body includes a biocompatible valve with a substantially cylindrical housing sized to fit the anatomic tract. The valve includes a first set of projections disposed circumferentially around an interior wall of the housing. A distal end of each of the projections in the first set of projections projects a first distance towards the center of the housing at a first angle relative to the wall of the housing.

IMPLANTABLE DEVICE FOR DIRECTIONAL CONTROL OF FLOW WITHIN THE ANATOMIC TRACTS OF THE BODY

CROSS-REFERENCE TO RELATED PATENT APPLICATIONS

This application claims priority from Provisional U.S. Patent Application 61/677,800, filed Jul. 31, 2012, which is incorporated herein by reference in its entirety.

BACKGROUND OF THE DISCLOSURE

Gastrointestinal Reflux Disease (GERD) is an increasingly common chronic condition, with clinical effects that range from mild intermittent discomfort following dietary indiscretion to severe chronic pain and increased risk of esophageal cancer. GERD affects an estimated 23-34% of the US population, with about 8% suffering severe or daily disruptive GERD. In addition to the discomfort produced by GERD, it is a demonstrable cause of the metaplastic condition known as Barrett's Esophagus, which has been shown to substantially increase the risk of esophageal cancer.

About 20% of patients with chronic GERD require long-term acid suppressive therapy and conservative estimates for proton pump inhibitor treatment failure suggest more than 1 million inadequately treated US patients. The most severe of these patients may undertake surgery, resulting in tens of thousands of major surgeries annually.

SUMMARY OF THE DISCLOSURE

According to one aspect of the disclosure, an implantable device for the directional control of flow through an anatomic tract of a body includes a biocompatible valve with a substantially cylindrical housing sized to fit the anatomic tract. The valve includes a first set of projections disposed circumferentially around an interior wall of the housing. A distal end of each of the projections in the first set of projections projects a first distance towards the center of the housing at a first angle relative to the wall of the housing.

In some implementations, the first set of projections form bristles and/or flaps. In certain implementations, the implantable device also includes a second set of projections disposed circumferentially around the interior wall of the housing. The second set of projections project into the center of the housing with a predetermined angle and length, which may differ from the angle and length at which the first set of projections projection into the device. In some implementations, the first and second set of projections are both configured to be flaps or bristles. In some other implementations, the two sets of projections are configured differently.

In some implementations, the second set of projections is rotationally offset from the first set of projections. In certain implementations, one or more surfaces of the device include a plurality of microstructures formed thereon. In some implementations, the microstructures are between about 100 μm and about 1 mm tall. In certain implementations, the microstructures are only formed on the bottom surface of at least one of the first and second set of projections.

In some implementations, the valve is configured to substantially impede the flow of fluid in a first direction but allows the flow of fluid in a second direction. The projections are at least partially flexible, and are configured to, in response to a force that exceeds a threshold, deform towards the mouth-facing end of the housing to allow passage of fluid in the second direction.

In yet other implementations, the device also includes an anchoring system to reversibly anchor the device to a patient's esophagus.

According to another aspect of the disclosure, a method for fabricating an implantable device for the directional control of flow through an anatomic tract of a body includes forming a mold for a valve. The valve is sized to fit the anatomic tract, and includes a first set of projections disposed circumferentially around an interior wall of a housing. A distal end of each of the projections in the first set of projections projects a first distance towards the center of the housing at a first angle relative to the wall of the housing. The method also includes injecting a biocompatible material into the mold, and then releasing the formed valve from the mold.

In some implementations, the method includes forming a microstructure pattern on at least one surface of the mold. The microstructure pattern is formed on the mold by micromachining or chemically etching the microstructure into the mold. In certain implementations, the method also includes coupling an anchoring system to the formed valve.

In yet another aspect of the disclosure, a method for preventing gastroesophageal reflux includes implanting a directional flow control device into a patient's esophagus. The control device includes a biocompatible valve with a housing sized to fit the patient's esophagus. The valve further includes a first set of projections disposed circumferentially around an interior wall of the housing. The end of each of the projections in the first set of projections projects a first distance towards the center of the housing at a first angle relative to the wall of the housing.

In some implementations, the valve also includes a second set of projections disposed circumferentially around the interior wall of the housing. The end of the projections in the second set project a second distance towards the center of the housing at a second angle relative to the first set of projections and the wall of the housing. In other implementations, the first set of projections has a plurality of microstructures formed thereon. In some implementations, the microstructures are between about 100 μm and about 1 mm tall. In certain implementations, the microstructures are only formed on the bottom surface of at least one of the first and second set of projections.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 2A-2C illustrate cut-away views of different example flap configurations suitable for use in the directional control valve of FIG. 1A.

FIGS. 4A and 4B illustrate cross-sectional views of different example bristle configurations suitable for use in the directional control valve of FIG. 1A.

FIGS. 8A-8C illustrate top views of example top ring configurations suitable for use in the directional control valve of FIG. 1A.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The systems and methods described herein relate generally to a device that enables the directional control of flow through an anatomical tract of the body. In some implementations, the device includes a plurality of projections that allow solids and fluids into a patient's stomach while substantially preventing a backflow of undesired fluids from the patient's stomach to the patient's esophagus. In certain implementations, the device allows the preferential backflow of healthy fluids and gases (e.g., gases caused by belching and fluids such as vomitus). As described below, in some implementations, the undesired fluids are fluids commonly associated with gastrointestinal reflux disease.

Figure 1A:
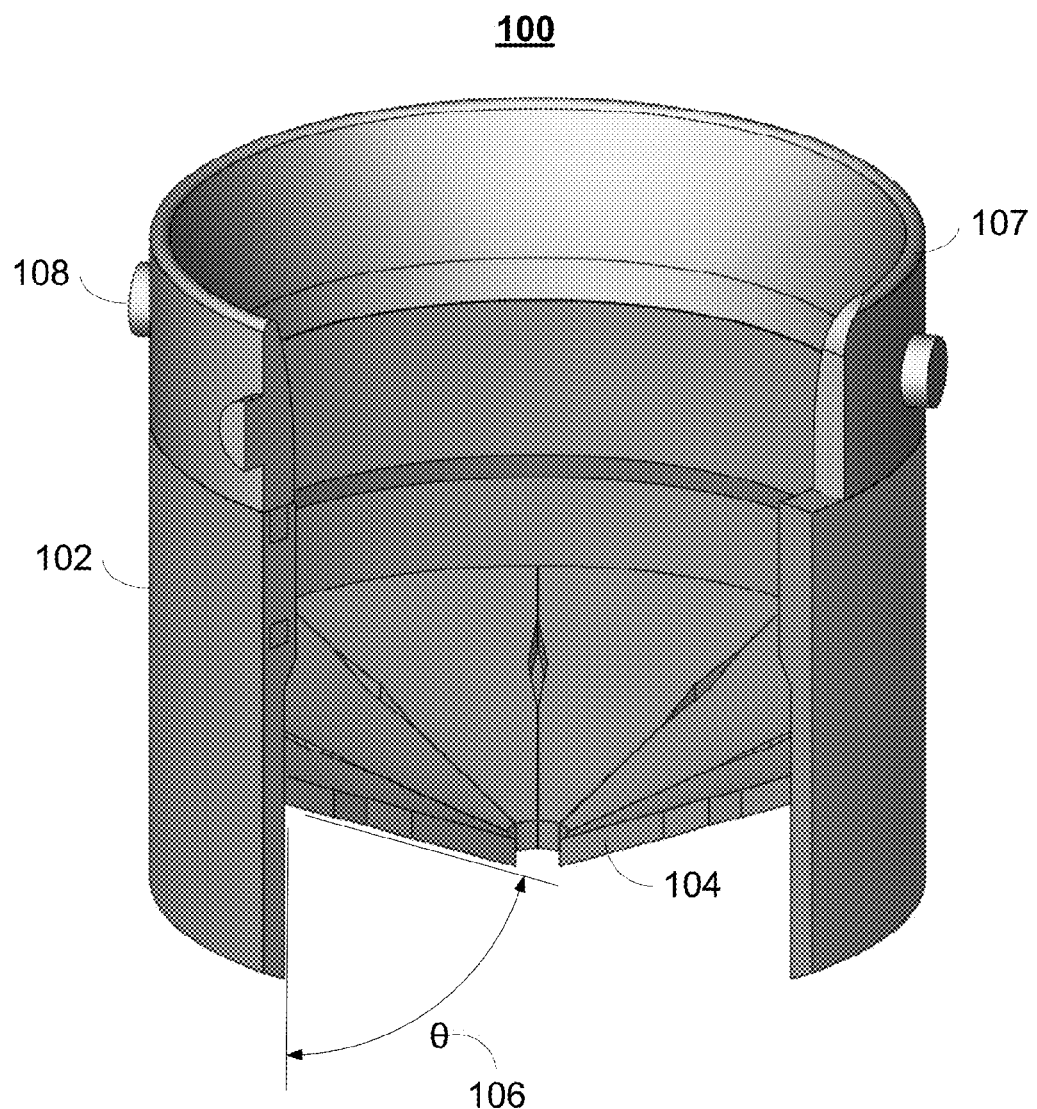
FIG. 1A illustrates an example directional control valve.

FIG. 1A illustrates a cut-a-way view of an example directional control valve 100. The directional control valve 100 includes a housing 102. Within the housing 102, a plurality of projections 104 project toward the central axis of the housing 102 at a predetermined angle 106. A plurality of anchors 108 are coupled to the exterior of the housing 102 to secure the directional control valve 100 within an anatomic tract.

The housing 102 provides the structure for the directional control valve 100. In some implementations, the directional control valve 100 is substantially cylindrical in shape. In other implementations, the housing 102 is frustoconical shaped or is shaped as an n-sided prism (e.g., a hexagonal or octagonal prism). In some implementations, the height of the housing 102 is about 0.5 cm-2 cm, about 1.5 cm-2.5 cm, about 2 cm-5 cm, or about 4.0 cm-7 cm. In some implementations, the external diameter of the housing 102 is about 1 cm-2 cm, about 1.5 cm-2.5 cm, about 2 cm-3 cm, or about 2.5 cm-4 cm. In some implementations, the directional control valve 100 is configured to be implanted in the esophagus or other anatomical tract of a patient. In some of these implementations, the diameter of the housing 102 is substantially equal to the inner diameter of the patient's esophagus (or other anatomical tract). As further described below in relation to the directional control valve's manufacture, the housing 102 is manufactured from a flexible and biocompatible material. For example, the directional control valve 100 and its components are manufactured from silicone, poly(dimethyl siloxane) (PDMS), polyurethane, polytetraflouroethylene (PTFE), or any combination thereof. In general, the material is selected such that the housing 102 can conform to the propulsive and other esophageal contractions present in the esophagus, is biocompatible, non-erosive, and/or non-biodegradable. In some implementations, the directional control valve 100 is manufactured from silicone because it is biocompatible and resists mechanical fatigue well (e.g., silicone withstands the wear and tear caused by the frequent movement of the projections 104).

In some implementations, an x-ray detectable element is embedded within the housing 102 (or other component of the directional control valve 100) to enable radiographical (or similar) detection of the directional control valve 100. For example, the directional control valve 100 can include a barium-sulfate element that is visible in standard x-ray radiographs.

In some implementations, the housing 102 includes a top ring 107. The top ring 107 is described further in relation to FIGS. 8A-8C. Briefly, the top ring 107 is configured to increase in diameter or decrease in diameter responsive to the expansion and contraction of the esophagus. In some implementations, the top ring 107 enables a single sized directional control valve to fit a variety of esophagus sizes. For example, the top ring 107 can be the widest part of the directional control valve 100. During the implantation procedure, a physician can expand the top ring 107 to fit the diameter of the current patient's esophagus. As the widest part of the directional control valve 100, in some implementations, the below described anchors 108 are coupled to the top ring 107.

Figure 7:
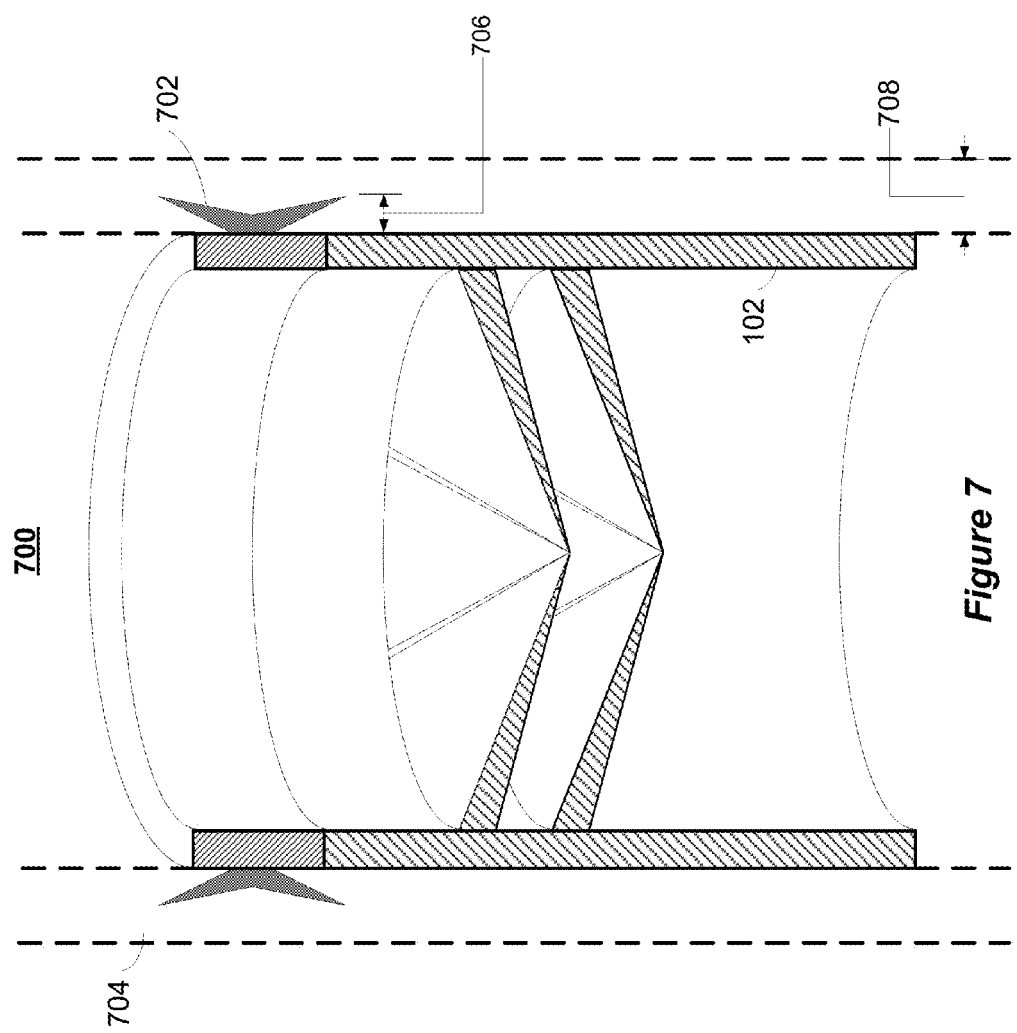
FIG. 7 illustrates a cross-sectional view of an example directional control valve implanted in an esophagus.

As further described in relation to FIG. 7, the exterior of the housing 102 includes a plurality of anchors 108. The anchors 108 are circumferentially disposed around the exterior of the housing 102. In some implementations, as illustrated in FIG. 1A, the anchors 108 are coupled to the top ring 107. In some implementations, the anchors 108 are coupled towards the top of the directional control valve 100. In the directional control valve 100, the anchors 108 are illustrated as posts. In other implementations, the anchors 108 are hooks, barbs, adhesive patches, eyelets for the placement of sutures, or any combination thereof. In some implementations, the directional control valve 100 includes between 2 and 5, between 5 and 10, or between 10 and 20 anchors.

The directional control valve 100 also includes a plurality of projections 104. The projections 104 are described in greater detail in relation to FIGS. 2-6, but briefly, the projections 104 project towards the central axis of the housing 102. The projections 104 are flaps that form a valve within the directional control valve 100. The valve formed by the projections 104 enables liquids and/or solids to flow into the stomach, but substantially prevents the flow of liquids out of the stomach and into the esophagus. For example, the projections 104 enable food to pass into the stomach, but substantially prevent gastric acid from escaping into the esophagus.

As illustrated in FIG. 1A, the projections 104 are wedge shaped. In other implementations, the projections 104 are posts or bristles coupled to the interior wall of the housing 102. In some implementations, the size of the projections 104 are varied such that the directional control valve 100 includes between 2-5, 5-10, 10-15, or 15-20 projections 104 within a circumferential row. As further described in relation to FIG. 6, in some implementations, the projections 104 and/or the interior wall of the housing 102 include a microstructure pattern.

In some implementations, the projections 104 control flow through selective deformation. The process of selective deformation is described in greater detail in relation to FIGS. 1B-1E. Briefly, the projections 104 control flow by deforming from an initially "closed" state in response to a force to an "open" state. The deformed projections 104 create a passage through the directional control valve 100. Once the force is removed from the projections 104, the projections 104 are configured to return substantially to their initial closed state. In some implementations, it requires a greater relative amount of force to deform the projections 104 in a first direction than it does in a second direction. For example, when the directional control valve 100 is implanted into an esophagus, the projections 104 are configured to allow solids and liquids to easily flow through the directional control valve 100 into the patient's stomach (i.e., the projections 104 deform relatively easily in the downward direction). However, the projections 104 are configured to substantially prevent the flow of gastric fluids out of the stomach and into the esophagus (i.e., it requires relatively more force to deform the projections 104 upward as when compared to the force required to cause the downward deformation). For example, the projections 104 can be configured to allow vomitus and gases created during belching to escape the stomach and enter the esophagus.

The projections 104 project into the housing 102 at a predetermined angle 106 with respect to the wall of the housing 102. In some implementations, the angle 106 is less than, greater than, or substantially equal to 90 degrees with respect to the wall of the housing 102. As described herein in relation to the projection angle 106, 90 degrees is orthogonal to the interior wall of housing 102. When implanted into a patient's esophagus, a projection angle of greater than 90 degrees projects the projections 104 rostrally towards the patient's head. A projection angle of less than 90 projects the projections 104 caudally towards the patient's stomach. In some implementations, the projections 104 project downward at an angle between about 90 degrees and about 75 degrees, about 75 degrees and about 50 degrees, about 50 degrees and 25 degrees, and about 25 degrees and 0 degrees.

The directional control valve 100, includes a single row of projections 104 circumferentially coupled to the interior of the housing 102. In some implementations, the directional control valve 100 includes a plurality of rows of projections 104. For example, the directional control valve 100 can include 2-5, 5-10, 10-15, or 15-20 rows of projections 104. Each row of projections 104 can be configured differently. For example, a directional control valve 100 can include a first row of bristle projections 104 and a second row of flap projections 104.

Figure 1B:
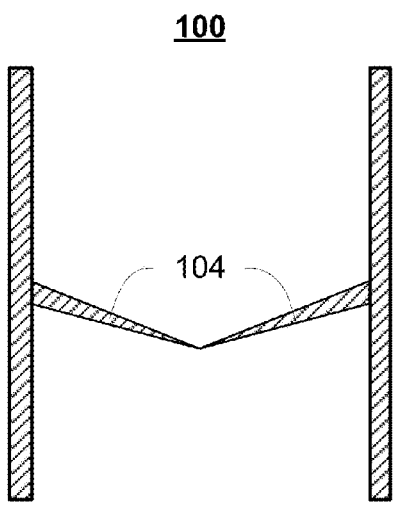
FIGS. 1B-1E illustrate the operation the example directional control valve from FIG. 1A.

FIGS. 1B-1E illustrate the operation of an example directional control valve. FIG. 1B is a cross-sectional view of the directional control valve 100 after deployment into a patient's esophagus (not shown). The directional control valve 100 is in its default state (i.e., no substantial forces are exerted on the projections 104 in the upward or downward direction) and the projections 104 form a substantially closed valve.

Figure 1C:
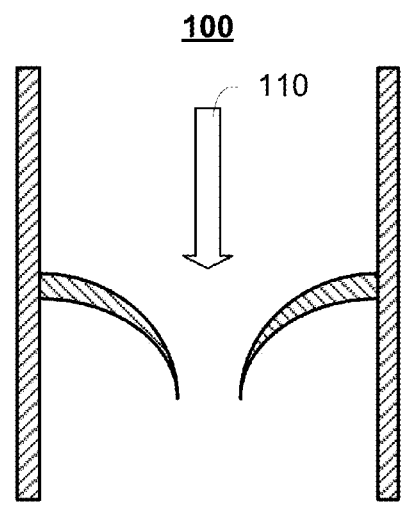

FIG. 1C is a cross-sectional view of the directional control valve 100 with a relatively low force 110 applied downward on the projections 104. Responsive to the force 110, the projections 104 deform downward to allow passage of the material imparting the force 110. For example, when a patient consumes solids and/or liquids the solids and/or liquids come into contact with the top surface of the projections 104 and cause the projections 104 to deform downward. The deformation of the projections 104 allows the passage of the solids and/or liquids into the patient's stomach. In some implementations, the imparted force 110 is generated by the weight of the solids and/or liquids and/or the propulsatory contractions of the esophagus. After the solids and/or liquids pass through the directional control valve 100 (resulting in the removal of the force 110 from the top surface of the projections 104), the projections 104 return substantially to their default position as illustrated in FIG. 1B.

Figure 1D:
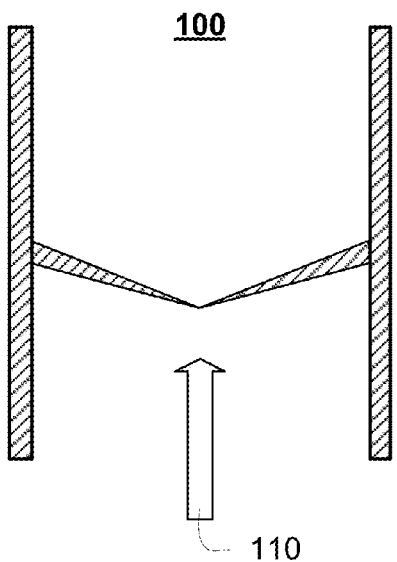

FIG. 1D is a cross-sectional view of the directional control valve 100 with the relatively low force 110 applied upward on the projections 104. FIG. 1D illustrates that the force 110, which causes the projections 104 to deform in a downward direction, is insufficient to cause substantial deformation of the projections 104 in an upward direction. For example, as the patient's esophageal sphincter relaxes, undesirable fluids may attempt to backflow into the patient's esophagus. In these implementations, the directional control valve 100 remains substantially closed and prevents the undesirable fluids from entering the patient's esophagus.

Figure 1E:
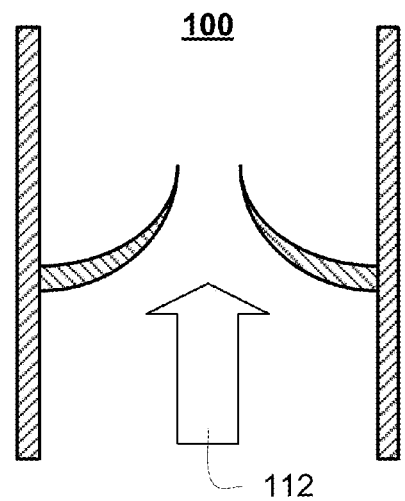

FIG. 1E is a cross-sectional view of the directional control valve 100 with the relatively high force 112 (as compared to the force 110) applied upward on the projections 104. During some instances, such as during emesis or belching, it is necessary for the stomach contents to reenter the esophagus in order to be expelled from the patient. In some implementations, the directional control valve is configured to allow such expulsions. In some implementations, vomitus, belching, and other medically necessary expulsions from the stomach induce a relatively high force 112 when compared to the force 110. When the bottom side of the projections 104 are exposed to the greater force 112, they deform upward. The upward deformation of the projections 104 allow vomitus and/or gas to pass through the directional control valve 100 and be expelled through the patient's mouth.

In some implementations, the projections 104 are "bi-stable." For example, the initial position of the projections 104 (as illustrated in FIG. 1B) is a first stable position. As described above, when deformed downward, the projections 104 substantially return to the initial position once the downward force is removed. In some implementations, the second stable position of the projections 104 is the upwardly deflected position (as illustrated in FIG. 1E). In bi-stable implementations, when the projections 104 are forced into the second stable position (i.e., the upward stable position) they remain in that position until a force is applied to the projections 104 that returns the projections 104 to their first stable position. In some implementations, the bi-stable nature of the projections enables a patient to fully expel vomitus and/or gas. For example, in some implementations, at the end phase of expelling vomitus and/or gas, the vomitus and/or gas may not have enough force to keep the projections 104 in the upward position. In a bi-stable implementation, the initial phase of the vomitus and/or gas release will open the valve, and it remains open, allowing for substantially complete expulsion of the vomitus and/or gas.

Figure 2A:
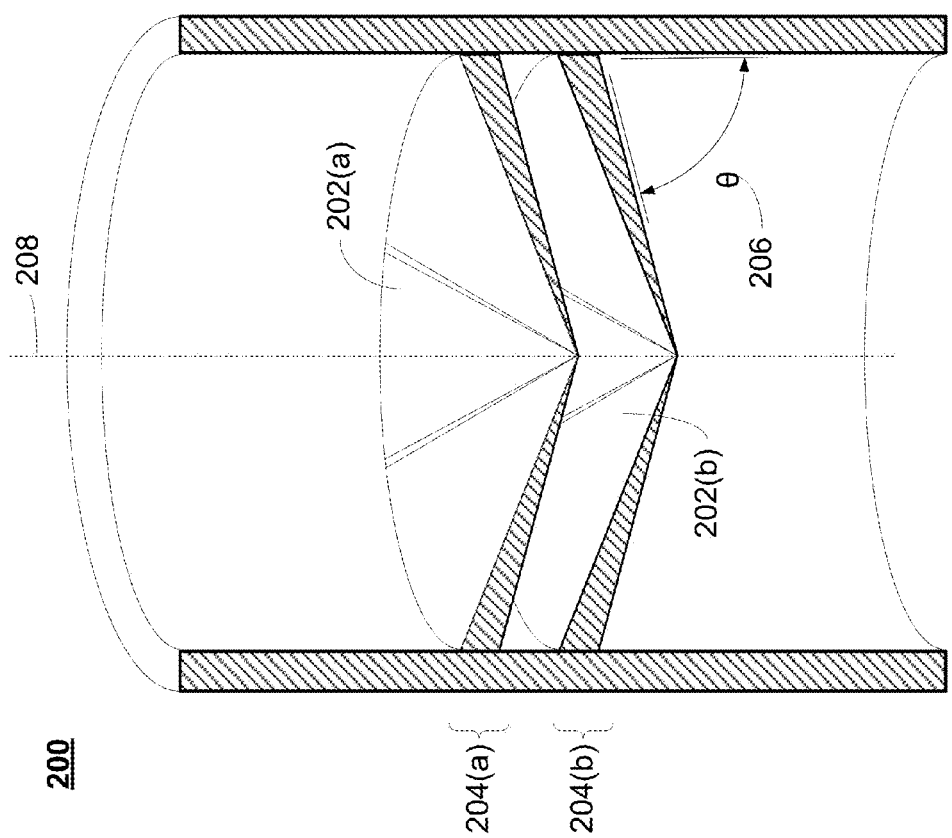
Figure 2B:
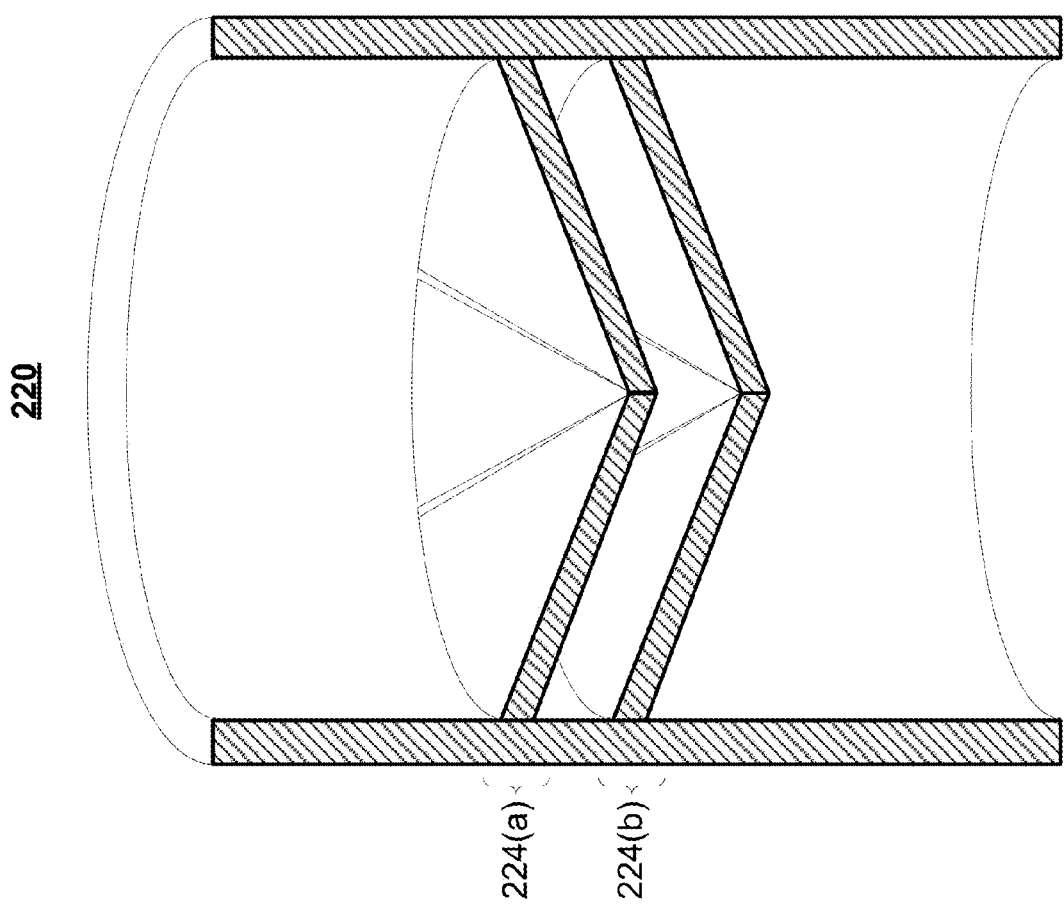

FIGS. 2A-2C illustrate different example flap configurations suitable for the projections used in a directional control valve, such as the projections 104 of then directional control valve 100 shown in FIG. 1. FIG. 2A illustrates a cross-sectional view of a directional control valve 200. The directional control valve 200 includes a plurality of projections 202(a) and a plurality of projections 202(b) (generally referred to as projections 202) projecting toward the central axis 208 of the directional control valve 200. The first plurality of projections 202(a) form a first row of projections 204(a) and the second plurality of projections 202(b) form a second row of projections 204(a). The projections 202 each project toward the central axis 208 of the directional control valve 200 at a predetermined angle 206. In some implementations, the projections 202 project toward the center of directional control valve 200 at different angles or have different lengths.

The thickness of the projections 202 gradually tapers towards the central axis 208 of the directional control valve 200. In some implementations, the thickness of the projections 202, the taper of the projections 202, angle of the projections 202, or a combination thereof is used to control the amount of force that is required to deform the projection 204. For example, in some implementations, a greater relative force is required to deform a thicker projections 204. In other implementations, projection width, length, shape, distribution, angle, density (i.e., the number of projections 204 in the directional control valve 100), or any combination thereof are used to "tune" the force required to deform the projections 204. For example, a first patient with more sever GERD may require a directional control valve that is "tuned" to require relatively more force to allow flow back into the esophagus when compared to a patient with less severe GERD.

In some implementations, the portion of the projections 202 nearest the wall of the housing experiences relatively more stress than the other portions of the projections 202. In some implementations, the increased thickness of the tapered projection near the wall improves the reliability (or lifespan) of the projections 202 without substantially increasing the force required to pass liquid or solids through the directional control valve 200. For example, by providing additional strength (in the form of additional material) near the wall of the housing, the projections' reliability is increased. However, moving towards the central axis 208 of the directional control valve 200, the projections' thicknesses taper. As the thickness of the projections tapers, the projections' flexibility increases when compared to the flexibility of the projections 202 near the wall of the housing. The increased flexibility reduces the amount of force required for solids, liquids, and gases to pass through the directional control valve 200.

In FIG. 2B, a second example directional control valve 220 includes another example projection configuration. The directional control valve 220 also includes two rows of projections 224(a) and 224(b) (generally referred to as projections 224). In contrast to the projections 204 in FIG. 2A, in which the thickness of the projections tapers towards a central axis of the directional control valve 220, each of the projections 224 has a substantially uniform thickness over substantially its entire surface area. FIG. 2C illustrates another example directional control valve 240. Unlike the directional control valves 200 and 220, the directional control valve 240 includes projections 244(a) and 244(b) that are normal to the central axis and the walls of the directional control valve housing.

Figure 3A:
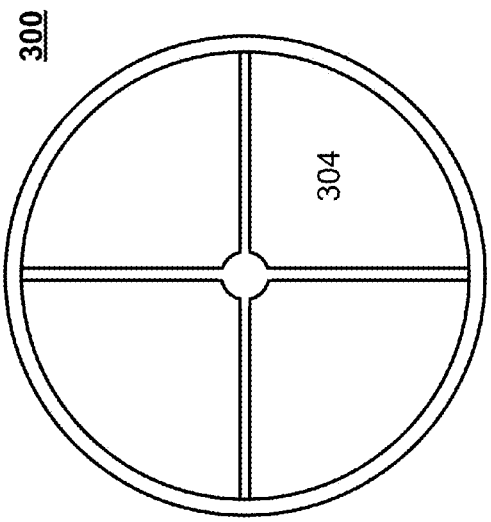
FIGS. 3A-3C illustrate top views of different example flap configurations suitable for use in the directional control valve of FIG. 1A.
Figure 3B:
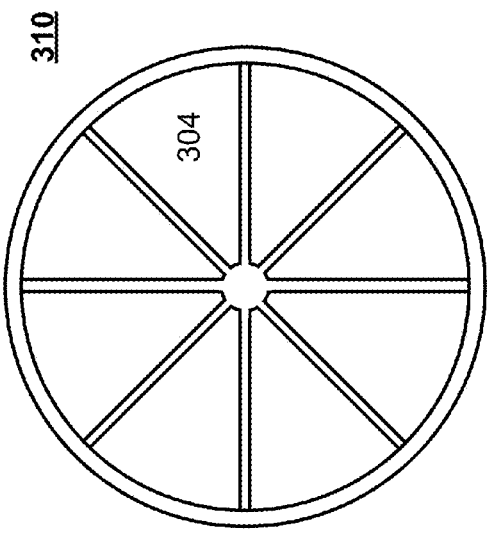
Figure 3C:
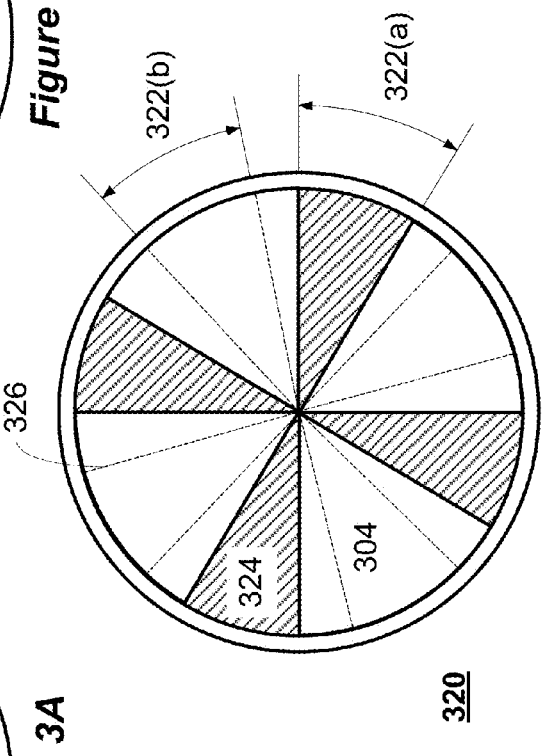

FIGS. 3A-3C illustrate top views of three example directional control valves. As described above, each row of projections includes a plurality of projections 304. The number of projections 304 within a row is configured responsive to the needs of the patient. For example, in some implementations, fewer, but larger projections 304 are used if a larger minimum relative force is desired to deflect the projections 304. In other implementations, more, but smaller projections 304 are used if a lower minimum force is desired to deflect the projections 304.

FIG. 3A illustrates a top view of the directional control valve 300. The directional control valve 300 includes four projections 304. As illustrated the four projections 304 of the directional control valve 300 do not fully project into the center of the directional control valve 300. In some implementations, the space created by not fully projecting to the center of the directional control valve 300 enables the release of gas from the patient's stomach.

FIG. 3B illustrates a top view of a directional control valve 310. The directional control valve 310 includes eight projections 304. In some implementations, it takes a relatively greater force to deform the projections 304 of directional control valve 300 when compared to the directional control valve 310. As described above, the number of projections 304 included in a directional control valve enables the directional control valve to be "tuned" to the needs of the patient. For example, a patient with a relatively weaker esophageal sphincter may have a directional control valve implanted that requires relatively greater force to enable re-flow back into the patient's esophagus.

FIG. 3C illustrates a top view of a directional control valve 320. Similar to the directional control valve 200, the directional control valve 320 includes a top row of projections and a second row of projections 324 (illustrated as shaded projections). The dashed lines 326 indicate the edges of the projections 324, which are obscured by the top row of projections 304. The directional control valve 320 includes a gap 322(a) between each of the projections 304 within the first row. The gap 322(a) exposes the projections 324 below the first row. The second row includes a gap 322(b) between each of the projections 324. As illustrated, the first row of projections and the second row of projections are rotationally offset with respect to one another. For example, the gap 322(a) between two projections 304 in the first row 202 aligns with a projection 324 in the second row. In other implementations, the rows of projections are rotationally offset but do not include gaps 322(a) and 322(b) between the individual projections 304 and 324. In yet other implementations, a first subset of the rows have gaps 322(a) between the projections 304 and a second subset of the rows do not have gaps 322(b) between projections. The directional control valve 320 also illustrates that in some implementations, the projections 304 reach to substantially the center of the directional control valve 320.

In some implementations, rotationally offsetting and/or including gaps between the projections of a directional control valve facilitates gas to be released from a patient's stomach (either through active belching or passive venting), while substantially preventing liquid from escaping back into the patient's esophagus from the stomach. In other implementations, rotationally offsetting the projections of the directional control valve increases the path length that a fluid or gas must traverse to escape a patient's stomach, thereby increasing the valve's resistance to stomach fluid back flow.

Figure 5B:
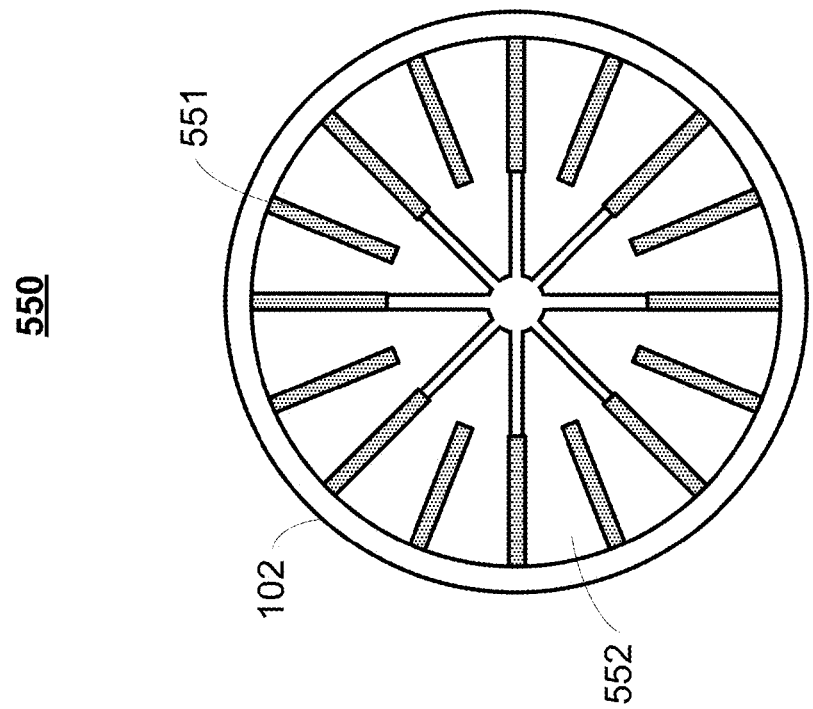
FIGS. 5A and 5B illustrate top views of an example bristle configuration suitable for use in the directional control valve of FIG. 1A.
Figure 5A:
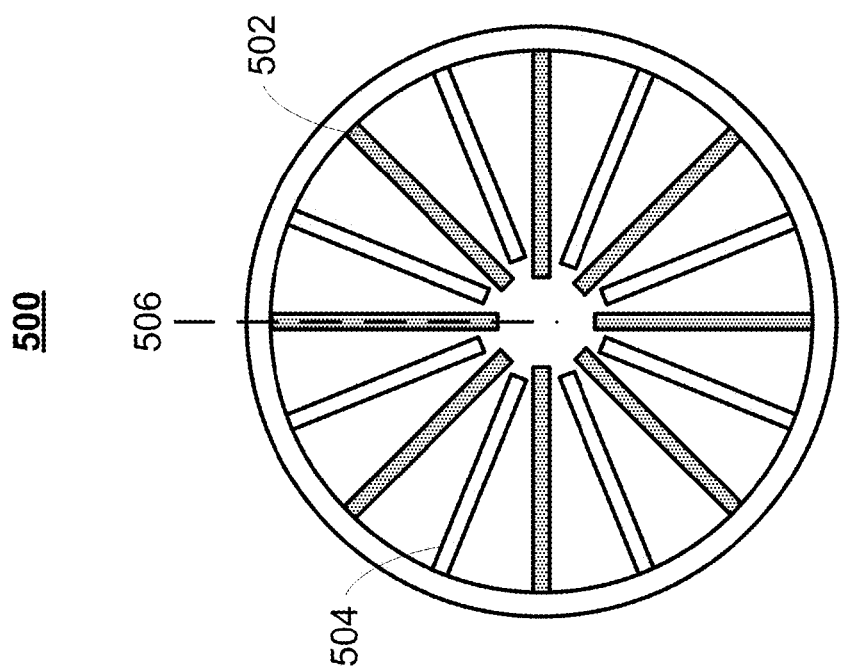

FIGS. 4A and 4B illustrate cross-sectional views of example bristle configurations suitable for use in a directional control valve. FIGS. 5A and 5B illustrate top views of example bristle distributions suitable for use with the bristle configurations illustrated in FIGS. 4A and 4B. The cross-sectional views of FIGS. 4A and 4B are made along the path 506 illustrated in FIG. 5. In FIGS. 4A, 4B, 5A and 5B, the projections form bristles (or posts) that project towards the central axis of the directional control valve.

Referring to FIG. 4A, a directional control valve 400 includes four rows of bristle shaped projections 402. Each row includes a plurality of bristle projections 402 circumferentially placed around the interior wall of the housing 102. The projections 402 project toward the central axis of the directional control valve 400 at a predetermined angle 406 with respect to the walls of the directional control valve housing 102. As described above, the angle 406 can be configured to be less than 90 degree, greater than 90 degrees, or substantially equal to 90 degrees with respect to the interior wall of the directional control valve 400. In some implementations, the directional control valve 400 includes projections 402 with varying angles 406. For example, a directional control valve can include at least two subsets of projections with angles 406 greater than 90 degrees, a second subset projections with angles 406 substantially equal to 90 degrees, and a third subset projections with angles 406 less than 90 degrees.

In some implementations, the bristle configured projections substantially slow, but do not prevent, the reflow of liquids back into the esophagus form the stomach. For example, experiments have shown that bristle-configured projections with an angle 406 less than 90 with respect to the interior wall of the housing 102 slow flow out of the stomach by a factor of 10 and bristle-configured projections with an angle 406 greater than 90 with respect to the interior wall of the housing 102 slow flow out of the stomach by a factor of 5 when compared to flow not impeded by a directional control valve. In some implementations, bristle configured projections provide preferential reverse flow of gas into the esophagus when compared to the reverse flow of solids and/or liquids.

The directional control valve 450 of FIG. 4B includes a plurality of projections also configured as bristles. The directional control valve 450 includes a first row 456 of projections 452 that are relatively longer than a second row 458 of projections 454. In some implementations, each row of projections includes projections of varying size. In some implementations, the projections 402, 452, and 454 of the directional control valves 400 and 450 are about 100 μm-1000 μm, about 500 μm-1.5 mm, about 1 mm-2 mm, about 1.5 mm-2.5 mm, or about 2 mm-3.5 mm. In some implementations, the projections 402, 452, and 454 project into substantially the center axis of the directional control valves 400 and 450. In yet other implementations, each row 456 and 458 of projections includes a different number of projections.

FIG. 5A illustrates a top view of a directional control valve 500. The directional control valve 500 includes a first row of projections and a second row of projections. The projections within the directional control valve 500 are configured as bristles similar to the bristle configurations described above in relation to FIGS. 4A and 4B. The projections 502 (i.e., the shaded bristles) are within a first row of projections, and the projections 504 (i.e., the unshaded bristles) are below the first row of projections and within a second row of projections below the first row of projections. The projections 504 within the second row of projections are rotationally offset from the projections 502 within the first row. In other implementations, the projections 502 and projections 504 are substantially aligned.

FIG. 5B illustrates a top view of an example directional control valve 550. The directional control valve 550 includes a first row of projections 551 configured as bristles. Beneath the first row of bristles (i.e., projections 551), the directional control valve 550 includes a circumferential row of projections 552 configured as flaps. In some implementations, the flap configured projections 552 and the bristle configured projections 551 are each configured to control the directional control of different substances. For example, in some implementations, the flap configuration may substantially inhibit the reflow of liquid back into to esophagus from the stomach and the bristle configuration may substantially inhibit the reflow of solids back into the esophagus from the stomach (except during times of belching or vomitus).

As indicated above, in some implementations, a microstructure pattern is formed on one or more of the surfaces of the directional control valve. In some implementations, the microstructure pattern is a plurality of pits, posts, ridges, or any combination thereof. In some implementations, a directional control valve only includes the microstructure pattern on the interior wall of the housing 102 and does not include the above described projections. In some implementations, the microstructure pattern creates a tortuous path for a liquid and/or solid to follow along as it moves through the directional control valve. The tortuous path, and subsequent longer path length created by the tortuous path, makes it relatively more difficult for liquids and/or solids to pass through the directional control valve 550.

Figure 6:
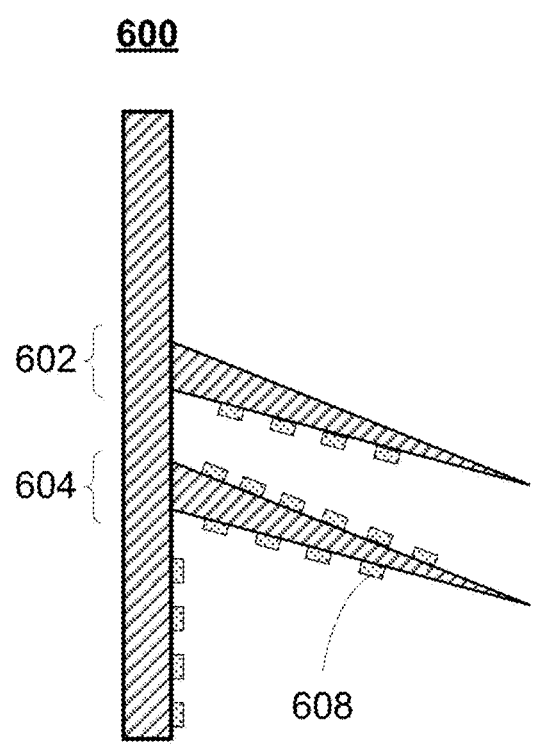
FIG. 6 illustrates a cross-sectional view of an example microstructure pattern suitable for use in the directional control valve of FIG. 1A.

FIG. 6 illustrates a cross-sectional view of an example microstructure pattern 608 and its placement in a directional control valve 600. The directional control valve 600 includes a first row of projections 602 and a second row of projections 604. The first row of projections 602 includes the microstructure pattern 608 on their downward facing surface. The second row of projections 604 includes the microstructure pattern on their upward and downward facing surfaces. The directional control valve 600 further includes the microstructure pattern 608 on the interior wall of the housing 102 below the second set of projections 604. In some implementations, the microstructure pattern 608 is configured to substantially affect a flow out of a patient's stomach without substantially affecting the flow into the patient's stomach. For example, placement of the microstructure pattern 608 on only the underside of the projections 604 and/or on the interior wall of the housing 102 below the projections 604 may impede flow back into the esophagus from the stomach without substantially affecting flow into the stomach. In some implementations, the height of the microstructure pattern 608 (relative to the surface of the projections 604) is about 10 μm-45 μm, about 25 μm-60 μm, about 40 μm-85 μm, or about 75 μm-100 μm. In some implementations, when the microstructure pattern 608 is longer than 100 μm it is referred to as a bristle configured projection, as described above.

The implementations of the projections and directional control valve configurations described herein are provided solely for illustrative purposes and not intended to limit the scope of the disclosure. One of ordinary skill in the art will recognize that aspects of the various projection and directional control valve configurations described above may be combined into a single directional control valve. For example, a directional control valve may include a first row with a first type of projections 104 and a second row with a second type of projections 104. In another example, different projections 104 configurations may be included within a single row.

FIG. 7 illustrates a cross-sectional view of a directional control valve 700 implanted into the esophagus 704 of a patient. The method for implanting the directional control valve 700 is described below in relation to FIGS. 11A-11C. As described above, the directional control valve 700 is held in place with a plurality of anchors 702. The plurality of anchors 702 are disposed circumferentially around the exterior of the directional control valve 700. In some implementations, the anchors 702 are deployable. For example, during implantation, the anchors 702 are initially retracted. The retracted state of the anchors 702 enables the directional control valve 700 to slide through an endoscopic deployment device or a patient's esophagus without snagging. Once in position, the anchors 702 deploy and secure the directional control valve 700 in place. In some implementations, the base of each anchor 702 is spring loaded such that it deploys upon exiting the endoscopic (or other) deployment device. In other implementations, the anchors 702 are not coupled to springs but have "shape memory" and self-deploy when not held in place by the endoscopic deployment device.

The anchors 702 extend from the housing 102 of the directional control valve 700 a distance 706. The distance 706 can be between about 1 mm and about 2 mm, about 2 mm and about 5 mm, and about 5 mm and about 10 mm. In some implementations, the distance 706 is selected to be less than the thickness 708 of the esophageal wall, which in the average adult is between about 5 mm and about 7 mm. In other implementations, the directional control valve 700 is secured within an anatomical tract of the patient with sutures instead of, or in addition to, the anchors 702.

FIGS. 8A-8C illustrate example implementations of the widest part of the directional control valve. As described above, in some implementations, the widest part of the directional control valve is the top ring 107 described above in relation to FIG. 1. The top ring allows the directional control valve to expand and/or contract responsive to the expansions and contractions of a patient's esophagus. The top ring also allows a directional control valve to fit different sized esophagi of different patients. In some implementations, an expandable top ring enables a single valve size to be to fit multiple esophagus sizes. The top ring 800, as illustrated in FIG. 8A, includes a lap joint. Similarly, FIG. 8B illustrates a top ring 810 with a "tongue and groove" joint. FIG. 8C illustrates a top ring 820 with an angle joint. In each of the top ring configurations 800, 810 and 820, a first portion of the top ring 801 slides past a second portion of the top ring 802 in direction 803. Movement of the first portion 801 in direction 803 reduces the diameter of the top ring.

Figure 9:
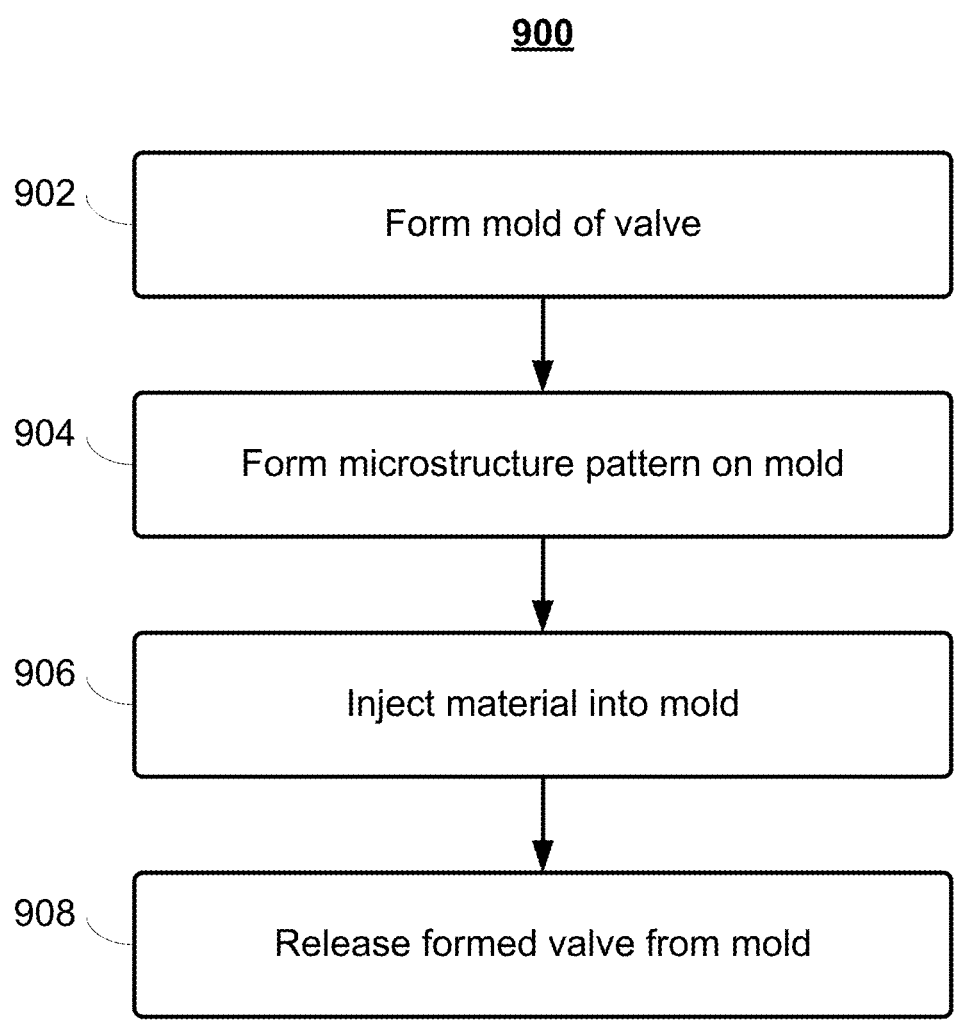
FIG. 9 illustrates a flow chart of an example method suitable for manufacturing the directional control valve of FIG. 1A.

FIG. 9 is a flow chart of an example method 900 for manufacturing a directional control valve. The method 900 begins with the formation of a directional control valve mold (step 902). Next, a microstructure pattern is formed on at least one surface the mold cavity (step 904). Then, a raw valve material is injected into the mold cavity (step 906). Once the raw material has substantially cured, the formed valve is released from the mold (step 908).

As set forth above, the method 900 of manufacturing a directional control valve begins with the formation of a mold (step 902). In some implementations, the method 900 is an injection molding process. In some implementations, the mold is fabricated through direct machining, a casting process, a rapid prototyping process (e.g., sterolithography), or any combination thereof. In some implementations, the mold is formed from beryllium-copper, steel, aluminum, or a photo-curable resin. In some implementations, the directional control valve 100 is molded as a single element, while in other implementations, the directional control valve 100 is molded as individual components (e.g., the projections are molded separately from the housing). The individual components are then assembled to form a complete directional control valve.

Next, a microstructure pattern is formed on at least one surface of the mold cavity (step 904). In some implementations, a negative of the microstructure pattern is formed in the mold cavity created in step 902 by micromachining the pattern onto the at least one surface of the mold cavity. In other implementations, a microstructure pattern is chemically etched into at least one surface of the mold cavity. In an alternative, or in some implementations, additional process, the microstructure pattern is formed on the components of the directional control valve following their removal from the injection mold. In implementations that employ casting of the mold in step 902, the microstructure pattern can be formed on the "positive" that is used to create the mold. In yet other implementations, step 904 is skipped such that the final directional control valve does not include a microstructure pattern.

After the manufacture of the one or more above described molds, a raw valve material is injected into the molds (step 906). The valve material is selected to be biocompatible. In some implementations, the raw material is a thermoplastic polymer, thermosetting polymer, or any of the above described materials. In one implementation, the raw material is liquid silicon rubber. As described above, in some implementations a radiographically visible material is added to the raw valve material. In some implementations, the components of the directional control valve are formed from different raw materials.

Responsive to injecting the raw material into the mold cavity, the formed directional control valve is released from the mold (step 908). In some implementations, after injection of the raw material into the mold cavity, the mold is cooled to solidify the molded directional control valve components. In some implementations, the raw material(s) are cured with the application of pressure, heat, light, and/or chemical curing agents. For example, the raw material can be cured with the process of vulcanization. Once sufficiently solid, the formed component of the directional control valve is removed from the mold.

Figure 10:
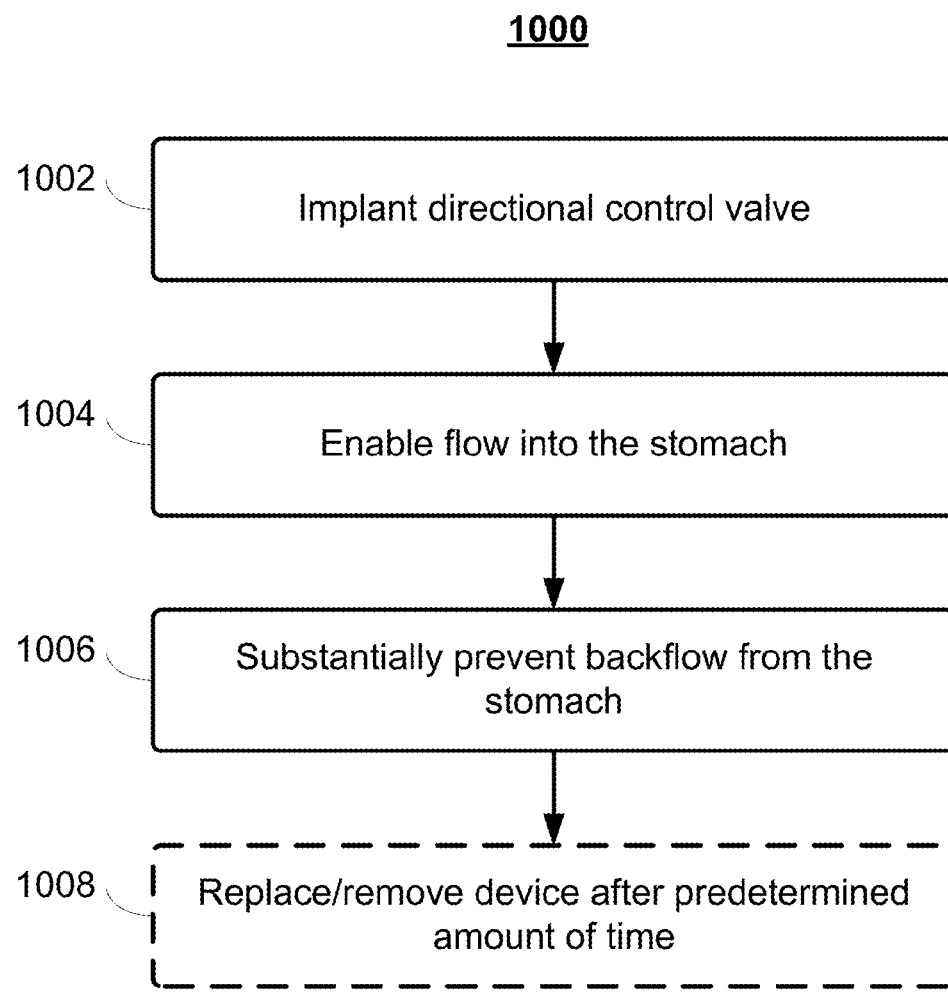
FIG. 10 illustrates a flow chart of an example method for preventing gastroesophageal reflux using the directional control valve of FIG. 1A.

FIG. 10 illustrates a flow chart of an example method 1000 for preventing gastroesophageal reflux. The method begins with the implantation of a directional control valve (step 1002). After implantation, flow is enabled into the stomach (step 1004) and the backflow of undesired fluids into the esophagus from the stomach is substantially prevented (step 1006). In some implementations, after a predetermined amount of time the directional control valve is removed (step 1008). One of ordinary skill in the art will recognize that similar method steps to those described in relation to method 1000 could be used in the bronchi to prevent aspiration, in the genitourinary system to prevent infection, in the vascular system, or within other anatomical tracts of the body in which one wishes to control flow.

Figure 11B:
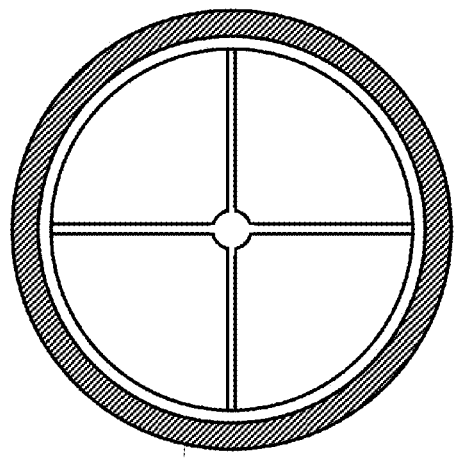
FIGS. 11A and 11B illustrate a cross-sectional view of a directional control valve in an example delivery device.
Figure 11C:
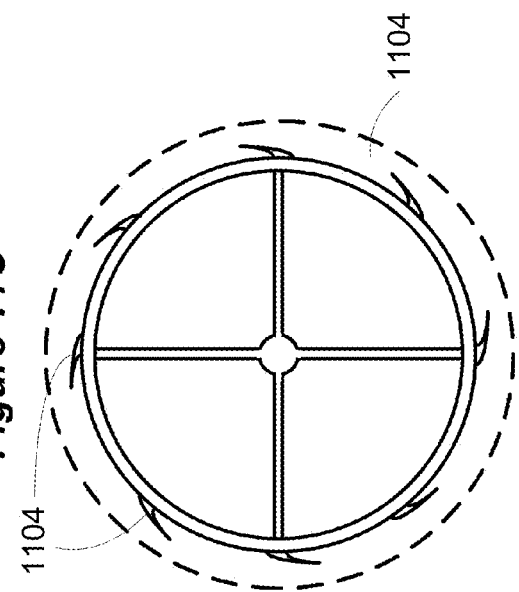
FIG. 11C is a top view of the directional control valve of FIGS. 11A and 11B after deployment into a patient's esophagus.
Figure 11A:
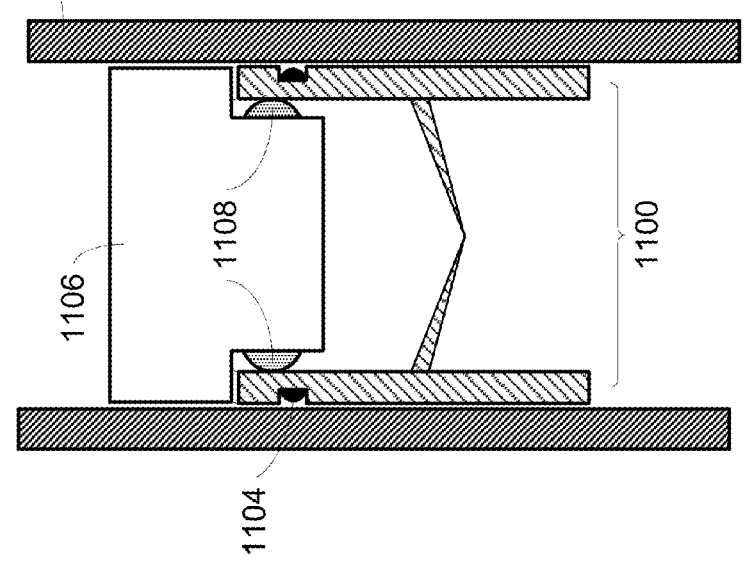

As set forth above, the method 1000 for preventing GERD begins with the implantation of a directional control valve (step 1002). In some implementations, the directional control valve is implanted to a patient's esophagus towards the patient's lower esophageal sphincter. FIGS. 11A-11C show greater detail regarding the implantation of the directional control valve.

FIG. 11A is a cross-sectional view of a directional control valve 1100 in an example delivery device 1102. In particular, the directional control valve 1100 is housed within the tip of an endoscopic delivery device 1102. FIG. 11A illustrates that the anchors 1104 are held in an un-deployed state by the interior wall of the delivery device 1102. The directional control valve 1100 is held in place within the tip of the endoscopic delivery device 1102 by a plunger 1106 and a plurality of bearings 1108.

FIG. 11B is a top view of the directional control valve 1100 within the endoscopic delivery device 1102 (with the plunger 1106 removed). As illustrated the, anchors 1104 are retracted (i.e., undeployed). When the anchors 1104 are retracted, a physician deploys the directional control valve 1100 by depressing the plunger 1106 at the control body of the endoscope. In some implementations, during deployment the directional control valve 1100 is rotated. In some implementations, the rotational motion of the directional control valve 1100 during deployment is caused by rifling on the interior wall of the endoscopic deliver device 1102. In other implementations, the plunger 1106 rotates when deploying the directional control valve 1100, thus also rotating the directional control valve 1100.

FIG. 11C is a top view of the directional control valve 1100 once deployed into a patient's esophagus. As described above the anchors 1104 are deployed into, but not through the esophageal wall 1110 of the patient. In some implementations, the interior wall of the endoscopic deployment device 1102 depresses the anchors 1104. The anchors 1104 spring outward (i.e., deploy) when not held in place by the walls of the endoscopic deployment device 1102. In some implementations, the above described rotational deployment of the directional control valve 1100 engages the anchors 1104 into the patient's esophageal wall 1110 securing the directional control valve 1100 in place.

Now referring back to the method 1000 of FIG. 10 and FIGS. 1B-1E, once the directional control valve is implanted, flow is enabled into the stomach (step 1004) and the backflow of undesired fluids into the esophagus from the stomach is substantially prevented (step 1006). As described above in relation to FIGS. 1B-1E, in some implementations the projections of the directional control valve are configured to enable flow into the stomach while substantially preventing re-flow out of the stomach and back into the esophagus. In some implementations, the undesirable fluids the directional control valve substantially prevents from entering the esophagus from the stomach include fluids responsible for GERD. For example, the fluids can include stomach acid, bile, and other enzymes and chemicals that cause GERD and/or inflammation of the esophagus. In some implementations, the directional control valve 1100 allows the passage of vomitus and gas from the stomach into the esophagus, where it can be expelled by the patient.

In some implementations, the directional control valve 100 is removed after a predetermined amount of time (step 1008). For example, the directional control valve 100 may be removed and replaced due to normal wear and tear resulting from the normal use of the directional control valve. For some patients, GERD is an acute condition (e.g., GERD caused by pregnancy or as a side effect to medication). In these cases, the directional control valve may be implanted during the acute presentation of GERD and be removed once the symptoms of GERD pass.

The invention may be embodied in other specific forms without departing from the spirit or essential characteristics thereof. The forgoing implementations are therefore to be considered in all respects illustrative, rather than limiting of the invention.

What is claimed:

1. An implantable device for a directional control of flow through an anatomic tract of a body, the device comprising:
   a biocompatible valve with a substantially cylindrical housing sized to fit the anatomic tract, the valve further comprising:
      a first set of flaps comprising a plurality of microstructures formed on a surface of the first set of flaps and configured to impede a first flow of fluid in a first direction, the first set of flaps disposed circumferentially around an interior wall of the housing, wherein a distal end of each of the flaps in the first set of flaps project a first distance towards a center of the housing at a first angle relative to the interior wall of the housing; and
      a second set of flaps disposed circumferentially around the interior wall of the housing, wherein a distal end of each of the flaps in the second set of flaps project a second distance towards the center of the housing at a second angle relative to the interior wall of the housing.

2. The device of claim 1, wherein the second set of flaps is rotationally offset from the first set of flaps.

3. The device of claim 1, wherein the second angle is equal to the first angle.

4. The device of claim 1, wherein the housing is configured such that when implanted, the housing includes a stomach-facing end and a mouth-facing end, and the first angle is less than 90 degrees with the distal ends of each of the flaps in the first set of flaps directed towards the stomach-facing end of the housing.

5. The device of claim 1, wherein the microstructures are between about 100 μm and about 1 mm long.

6. The device of claim 1, wherein the microstructures are only formed on portions of a bottom surface of the first set of flaps.

7. The device of claim 1, wherein the valve is configured to substantially impede the first flow of fluid in a first direction but allows a second flow of fluid in a second direction.

8. The device of claim 7, wherein the first set of flaps are at least partially flexible, and are configured to, in response to a force that exceeds a threshold, deform towards a mouth-facing end of the housing to allow passage of fluid in the first direction.

9. The device of claim 1, further comprising an anchoring system to reversibly anchor the device to the anatomic tract.

10. The device of claim 1, wherein the anatomic tract is an esophagus.

11. The device of claim 1, wherein a height of the device is between about 1 cm and about 4 cm and a width of the device is between about 2 cm and about 3 cm.

12. The device of claim 1, wherein the first set of flaps and the second set of flaps each have a plurality of microstructures formed thereon.

* * * * *